United States Patent
Resconi et al.

(10) Patent No.: US 7,417,006 B2
(45) Date of Patent: Aug. 26, 2008

(54) CATALYST SYSTEM FOR THE POLYMERIZATION OF OLEFINS

(75) Inventors: Luigi Resconi, Ferrara (IT); Simona Guidotti, Malalbergo-Altedo-Bologna (IT)

(73) Assignee: Basell Polyolefine GmbH, Wesseling (DE)

( * ) Notice: Subject to any disclaimer, the term of this patent is extended or adjusted under 35 U.S.C. 154(b) by 393 days.

(21) Appl. No.: 10/478,346

(22) PCT Filed: May 7, 2002

(86) PCT No.: PCT/EP02/05087

§ 371 (c)(1),
(2), (4) Date: Nov. 21, 2003

(87) PCT Pub. No.: WO02/102811

PCT Pub. Date: Dec. 27, 2002

(65) Prior Publication Data

US 2004/0132612 A1    Jul. 8, 2004

(30) Foreign Application Priority Data

May 21, 2001    (EP)    ................... 01201904

(51) Int. Cl.
*C07D 207/00*    (2006.01)
*C07D 209/00*    (2006.01)
*B01J 31/00*    (2006.01)
*B01J 37/00*    (2006.01)
*C08F 4/02*    (2006.01)
*C08F 4/44*    (2006.01)

(52) U.S. Cl. .................. 502/155; 548/402; 548/405; 502/103; 502/117; 502/152; 502/167; 502/168; 502/172; 526/132; 526/134; 526/135; 526/163

(58) Field of Classification Search ................ 548/402, 548/405; 502/103, 117, 152, 155, 167, 168, 502/172; 526/132, 134, 135, 163
See application file for complete search history.

(56) References Cited

U.S. PATENT DOCUMENTS

| | | | | |
|---|---|---|---|---|
| 5,145,819 | A | 9/1992 | Winter et al. | 502/117 |
| 5,239,022 | A | 8/1993 | Winter et al. | 526/127 |
| 5,243,001 | A | 9/1993 | Winter et al. | 526/127 |
| 5,324,800 | A | 6/1994 | Welborn, Jr. et al. | 526/160 |
| 5,384,299 | A | 1/1995 | Turner et al. | 502/155 |
| 5,556,928 | A | 9/1996 | Devore et al. | 526/127 |
| 6,608,224 | B2 * | 8/2003 | Resconi et al. | 556/27 |
| 2006/0094840 | A1 * | 5/2006 | Resconi et al. | 526/160 |

FOREIGN PATENT DOCUMENTS

| | | |
|---|---|---|
| EP | 0129368 | 12/1984 |
| EP | 0416815 | 3/1991 |
| EP | 0420436 | 4/1991 |
| EP | 0485820 | 5/1992 |
| EP | 0485822 | 5/1992 |
| EP | 0485823 | 5/1992 |
| EP | 0643066 | 3/1995 |
| EP | 0671404 | 9/1995 |
| WO | 9102012 | 2/1991 |
| WO | 9104257 | 4/1991 |
| WO | 9622995 | 8/1996 |
| WO | 9623010 | 8/1996 |
| WO | 9627439 | 9/1996 |
| WO | 9702298 | 1/1997 |
| WO | 9822486 | 5/1998 |
| WO | 9840374 | 9/1998 |
| WO | 9921899 | 5/1999 |
| WO | 9924446 | 5/1999 |
| WO | 9942467 | 8/1999 |
| WO | 9958539 | 11/1999 |
| WO | 0035973 | 6/2000 |

OTHER PUBLICATIONS

M. Brookhart et al., "Highly Active Iron and Cobalt Catalysts for the Polymerization of Ethylene;" *J. Am. Chem. Soc.*, 120, p. 4049-4050 (1998).
M. Brookhart et al., "New Pd(II)- and Ni(II)-Based Catalysts for Polymerization of Ethylene and α-Olefins;" *J. Am. Chem. Soc.*, 117, p. 6414-6415 (1995).
M. Brookhart et al., "Copolymerization of Ethylene and Propylene with Functionalized Vinyl Monomers by Palladium(II) Catalysts;" *J. Am. Chem. Soc*; 118, p. 267-268 (1996).
V. Gibson et al., "Novel olefin polymerization catalysts based on iron and cobalt;" *Chem. Commun.*, p. 849-851 (1998).
F. Jäger et al., "Metallacyclodisiladiazanes of Titanium and Zirconium; Synthesis, Structure and Polymerization Studies;" *Chem. Ber./Recueil*, 130, p. 399-403 (1997).
G. Kehr et al., "Protonation of the Heterocyclic Cp-Anion Equivalent [Pyrrolyl-B(C$_6$F$_5$)]Li-Formation of a Useful Neutral Bronsted Acid for the Generation of Homogeneous Metallocene Ziegler Catalysts", *Eur. J. Inorg. Chem.*, p. 535-538 (2001).

* cited by examiner

*Primary Examiner*—Aileen Felton
*Assistant Examiner*—J. Eric McDonough
(74) *Attorney, Agent, or Firm*—Jarrod N Raphael

(57) ABSTRACT

A salt of formula (I)

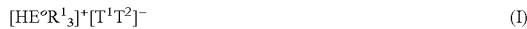

wherein $E°$ is a nitrogen or phosphorous atom; $R^1$ is hydrocarbon radical; $T^1$ is a Lewis acid that forms a complex with $T^2$, and $T^2$ is a substituted pyrrolyl radical of formula (III)

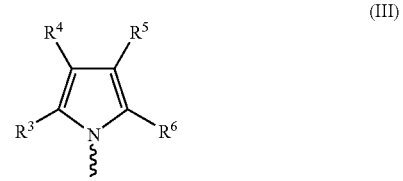

These salts can be used as cocatalyst in a process for the polymerization of alpha-olefins in conjunction with a transition metal organometallic compound.

12 Claims, No Drawings

CATALYST SYSTEM FOR THE POLYMERIZATION OF OLEFINS

This application is the U.S. national phase of International Application PCT/EP02/05087, filed May 7, 2002.

FIELD OF THE INVENTION

The present invention relates to salts and catalyst systems for the polymerization of olefins comprising such salts. The invention also relates to a process for the polymerization of olefins carried out in the presence of the above catalyst systems.

PRIOR ART DISCLOSURE

Homogeneous catalytic systems based on metallocene complexes are known to be active in the polymerization of olefins; said complexes must be activated by means of suitable cocatalytic compounds. The first generation of cocatalysts developed for homogeneous metallocene olefin polymerization consisted of alkyl aluminum chlorides ($AlR_2Cl$), wherein substituents R are preferably methyl or ethyl; these cocatalysts exhibit low ethylene polymerization activity levels and negligible propylene polymerization activity.

The second generation of cocatalyst systems comprised the class of alkylalumoxanes, commonly obtained by reacting trialkyl aluminum compound and water in a molar ratio of 1:1 to 100:1; these alumoxanes are oligomeric linear and/or cyclic compounds represented by the formulae:

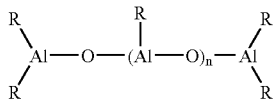

for linear oligomeric alumoxanes, and

for cyclic oligomeric alumoxanes, wherein the substituents R are usually methyl, ethyl or isobutyl groups, n ranges from 0 to 40, and m ranges from 3 to 40. Methylalumoxane (MAO) is the most widely used cocatalyst. Nevertheless alkylalumoxanes, and in particular methylalumoxane, though very active in metallocene-based catalyst systems, exhibit several inherent problems in use, such as the need for high alumoxane/metallocene molar ratios to produce satisfactory catalytic activities, their high reactivity toward impurities (moisture, alcohols etc.) and their easy flammability. Moreover, it has not been possible to isolate characterizable metallocene active species using MAO. Accordingly, some of the developments in this area involved a search for alternative cocatalysts.

$B(C_6F_5)_4^-$ types of non-coordinating anions have been developed as cocatalysts for metallocene-based systems. More specifically, these activators are ion-exchange compounds comprising a trialkyl or dialkylammonium cation, which will irreversibly react with a metallocene, and a fluorinated arylborate anion, capable of stabilizing the metallocene cation complex and sufficiently labile to permit displacement by the monomer during polymerization (see for instance WO 91/02012). In particular, they have the advantage of being used in a 1:1 catalyst-cocatalyst ratio. Therefore, it is usually not necessary to remove the small amount of boron from the final polymer, unlike the aluminum-based cocatalysts mentioned above. As preferred activators are tri(n-butyl)ammonium tetrakis(pentafluorophenyl)boron and N,N-dimethylanilinium tetrakis(pentafluorophenyl)boron.

These cocatalysts exhibit high catalytic activities but, from a synthetic point of view, the industrial production of these cocatalysts is quite expensive.

WO 99/42467 discloses a catalyst activator of general formula $(A^{1+a})_b(Z^1J^1_j)^{-c}_d$ wherein $A^1$ is a cation of charge +a; $Z^1$ is an anion group of from 1 to 50, preferably 1 to 30 atoms, not counting hydrogen atoms, further containing two or more Lewis base sites; $J^1$ independently each occurrence is a Lewis acid coordinated to at least one Lewis base site of $Z^1$, and optionally two or more such $J^1$ groups may be joined together in a moiety having multiple Lewis acidic functionality; j is a number from 2 to 12 and a, b, c and d are integers from 1 to 3, with the proviso that a×b is equal to c×d. One of preferred group Z is imidazole and its derivatives. The drawback of these catalyst activators is that one equivalent of activator contains two equivalents of the Lewis acid that usually is the most expensive part of the activator. The Applicant has now found a new class of olefin polymerization cocatalysts, which reduces the use of excess of cocatalyst with respect to alkylaluminoxanes.

The present invention concerns a salt of formula (I):

$$[HE^\circ R^1_3]^+[T^1T^2]^- \qquad (I)$$

wherein $E^\circ$ is a nitrogen (N) or phosphorous (P) atom; preferably $E^\circ$ is nitrogen; $R^1$, equal to or different from each other, is selected from the group consisting of linear or branched, saturated or unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^1$ can form one $C_4$–$C_7$ ring, optionally containing O, S, N, P or Si atoms, that can bear substituents; preferably $R^1$ a linear or branched, saturated or unsaturated, $C_1$–$C_{30}$ alkyl radical; $T^1$ is a Lewis acid, that form a complex with $T^2$, $T^1$ having formula (II)

$$MtR^2_3 \qquad (II)$$

wherein Mt is a metal belonging to Group 13 of the Periodic Table of the Elements (IUPAC); $R^2$, equal to or different from each other, are selected from the group consisting of halogen, halogenated $C_6$–$C_{20}$ aryl and halogenated $C_7$–$C_{20}$ alkylaryl groups; two $R^2$ groups can also form with the metal Mt one condensed ring, such as for example 9-borafluorene compounds.

Preferably Mt is B or Al, and more preferably is B; the substituents $R^2$ are preferably selected from the group consisting of $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; most preferred $R^2$ substituents are $C_6F_5$ radicals; $T^2$ is a moiety of formula (III) bonding $T^1$ through the nitrogen atom

wherein $R^3$, $R^4$, $R^5$ and $R^6$, equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that can bear substituents; with the proviso that at least one of the $R^3$, $R^4$, $R^5$ and $R^6$ is different from hydrogen.

Preferred moiety of formula (III) are those belonging to formula (IV)

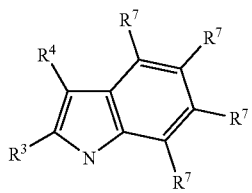

(IV)

wherein the substituents $R^3$ and $R^4$ have the meaning reported above and the substituents $R^7$, equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups optionally containing O, S, N, P, Si or halogen atoms, or two or more adjacent substituents $R^7$ form one or more $C_4$–$C_7$ rings optionally containing O, S, N, P or Si atoms, said rings can bear substituents; preferably $R^7$, equal to or different from each other, are selected from the group consisting of hydrogen, halogen, linear or branched, saturated or unsaturated $C_1$–$C_{10}$ alkyl optionally containing O atoms. Preferably $R^3$ and $R^4$ are hydrogen.

Non limitative examples of anion $[T^1T^2]^-$ are:
[tris(pentafluorophenyl)2-ethylpyrrolyl]borate; [tris(pentafluorophenyl)2,4-dimethylpyrrolyl]borate; [tris(pentafluorophenyl)2,5-dimethylpyrrolyl]borate; [tris(pentafluorophenyl)4,5,6,7-tetrahydroindolyl]borate; [tris(pentafluorophenyl)1,2,5-trimethylpyrrolyl]borate; [tris(pentafluorophenyl)2,4-dimethyl-3-ethylpyrrolyl]borate; [tris(pentafluorophenyl)]borate; [tris(pentafluorophenyl indolyl)]borate; [tris(pentafluorophenyl)2-methylindolyl]borate; [tris(pentafluorophenyl)3-methylindolyl]borate; [tris(pentafluorophenyl)4-methylindolyl]borate; [tris(pentafluorophenyl)5-methylindolyl]borate; [tris(pentafluorophenyl)6-methylindolyl]borate; [tris(pentafluorophenyl)7-methylindolyl]borate; [tris(pentafluorophenyl)2,3-dimethylindolyl]borate; [tris(pentafluorophenyl)2,5-dimethylindolyl]borate; [tris(pentafluorophenyl)5-fluoroindolyl]borate; [tris(pentafluorophenyl)4-chloroindolyl]borate; [tris(pentafluorophenyl)5-chloroindolyl]borate; [tris(pentafluorophenyl)6-chloroindolyl]borate; [tris(pentafluorophenyl)5-chloro-2-methylindolyl]borate; [tris(pentafluorophenyl)5-bromoindolyl]borate; [tris(pentafluorophenyl)5-methoxyindolyl)]borate; [tris(pentafluorophenyl)4-methoxyindolyl]borate; [tris(pentafluorophenyl)5,6-dimethoxyindolyl]borate; [tris(pentafluorophenyl)5-benzyloxyindolyl]borate; [tris(pentafluorophenyl)2-ethylpyrrolyl]alumate; [tris(pentafluorophenyl)2,4-dimethylpyrrolyl]alumate; [tris(pentafluorophenyl)2,5-dimethylpyrrolyl]alumate; [tris(pentafluorophenyl)4,5,6,7-tetrahydroindolyl]alumate; [tris(pentafluorophenyl)1,2,5-trimethylpyrrolyl]alumate; [tris(pentafluorophenyl)2,4-dimethyl-3-ethylpyrrolyl]alumate; [tris(pentafluorophenyl)]alumate; [tris(pentafluorophenyl indolyl)]alumate; [tris(pentafluorophenyl)2-methylindolyl]alumate; [tris(pentafluorophenyl)3-methylindolyl]alumate; [tris(pentafluorophenyl)4-methylindolyl]alumate; [tris(pentafluorophenyl)5-methylindolyl]alumate; [tris(pentafluorophenyl)6-methylindolyl]alumate; [tris(pentafluorophenyl)7-methylindolyl]alumate; [tris(pentafluorophenyl)2,3-dimethylindolyl]alumate; [tris(pentafluorophenyl)2,5-dimethylindolyl]alumate; [tris(pentafluorophenyl)5-fluoroindolyl]alumate; [tris(pentafluorophenyl)4-chloroindolyl]alumate; [tris(pentafluorophenyl)5-chloroindolyl]alumate; [tris(pentafluorophenyl)6-chloroindolyl]alumate; [tris(pentafluorophenyl)5-chloro-2-methylindolyl]alumate; [tris(pentafluorophenyl)5-bromoindolyl]alumate; [tris(pentafluorophenyl)5-methoxyindolyl)]alumate; [tris(pentafluorophenyl)4-methoxyindolyl]alumate; [tris(pentafluorophenyl)5,6-dimethoxyindolyl]alumate; [tris(pentafluorophenyl)5-benzyloxyindolyl]alumate; and the compounds wherein the group pentafluorophenyl is replaced with heptafluoronaphthyl; 2,3,5,6,7,8-hexafluoronaphthyl; 2,4,5,6,7,8-hexafluoronaphthyl; 3,4,5,6,7,8-hexafluoronaphthyl; 2,3,4,6,7,8-hexafluoronaphthyl; 2,3,4,5,7,8-hexafluoronaphthyl; 2,3,5,6,7,8-hexafluoro-4-methylnaphthyl; 2,4,5,6,7,8-hexafluoro-3-methylnaphthyl; 3,4,5,6,7,8-hexafluoro-2-methylnaphthyl; 2,3,4,6,7,8-hexafluoro-5-methylnaphthyl; 2,3,4,5,7,8-hexafluoro-6-methylnaphthyl; nonafluorobiphenyl; 2,2',3,3',5,5',6,6'-octafluorobiphenyl; 3,3',4,4',5,5',6,6'-octafluorobiphenyl; 2,2',4,4',5,5',6,6'-octafluorobiphenyl; 2,2',3,3',4,4',6,6'-octafluorobiphenyl; 2,2',3,3',4,4',5,5'-octafluorobiphenyl; 2,2',3,3',5,5',6,6'-octafluorobiphenyl; 3,3',4,4',5,5',6,6'-octafluorobiphenyl; 2,2',4,4',5,5',6,6'-octafluorobiphenyl; 2,2',3,3',4,4',6,6'-octafluoro-5,5'-methylbiphenyl; 2,2',3,3',4,4',5,5'-octafluoro-6,6'-methylbiphenyl; 2,2',3,3',5,5',6,6'-octafluoro-4,4'-biphenyl; 3,3',4,4',5,5',6,6'-octafluoro-2,2'-biphenyl; 2,2',4,4',5,5',6,6'-octafluoro-3,3'-biphenyl; 2,3,4,6-tetrafluorophenyl; 2,3,5,6-tetrafluorophenyl; 2,3,5-trifluorophenyl, 2,3,6-trifluorophenyl; 1,3-difluorophenyl, 2,3,5,6-tetrafluoro-4-methylphenyl; 2,3,4,6-tetrafluoro-5-methylphenyl; 2,6-difluoro-3-methylphenyl; 2,4-difluoro-5-methylphenyl; 3,5-difluoro-2-methylphenyl; fluorobis(pentafluorophenyl); chlorobis(pentafluorophenyl); dichloro(pentafluorophenyl) and difluoro (pentafluorophenyl); and the compounds indolyl 9-chloro-9-borateperfluorofluorene; indolyl 9-methyl-9-borateperfluorpfluorene; indolyl 9-pentafluorophenyl-9-borateperfluorofluorene and indolyl 9-bromo-9-borateperfluorofluorene.

Non limitative examples of moiety $HE°R^1_3$ are:
trimethylammonium; triethylammonium; tripropylammonium; tri(n-butyl)ammonium; methyldi(octadecyl)ammonium; N,-methylanilinium; N-ethylanilinium; N-methyl (2,4,6-trimethyl)anilinium; and methyldicyclohexylammonium.

The salt object of the present invention can easily be prepared by contacting in any order i) about one equivalent of a compound of formula (V)

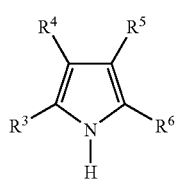

(V)

wherein $R^3$, $R^4$, $R^5$ and $R^6$ are described above;

ii) about one equivalent of a Lewis acid of formula (II)

$MtR^2_3$ (II)

wherein Mt and $R^2$ are described above; and iii) about one equivalent of a compound of formula $E°R^1_3$ wherein $E°$ and $R^1$ have been described above.

A preferred process comprises the following steps:

a) contacting about one equivalent of a compound of formula (V)

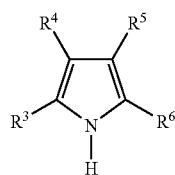

wherein $R^3$, $R^4$, $R^5$ and $R^6$ are described above; with one equivalent of a Lewis acid of formula (II)

$$MtR^2_3 \qquad (II)$$

wherein Mt and $R^2$ are described above; and b) optionally isolating the reaction product of step a) and then adding about one equivalent of a compound of formula $E°R^1_3$ wherein $E°$ and $R^1$ have been described above.

The two steps described above can be carried out both by isolating the intermediate product formed in step a), generally by filtration or evaporation of the solvent, or carried out "one pot" without isolating the intermediate product, preferably the reaction is carried out in an aprotic solvent, even more preferably in a polar aprotic solvent (such as toluene, diethyl ether or $CH_2Cl_2$), at room temperature. The reaction can be carried out also in the presence of little amount of water, preferably equal to or less than one molar equivalent with respect to the Lewis acid.

The final product is generally isolated by filtration or evaporation of the solvent.

It is another object of the present invention a catalyst system for the polymerization of olefins comprising the product obtainable by contacting:

(A) at least one transition metal organometallic compound, and, (B) salt of formula (I)

$$[HE°R^1_3]^+[T^1T^2]^- \qquad (I)$$

wherein $E°$, $R^1$, $T^2$ and $T^1$ have been described above; and (C) optionally an alkylating agent.

Transition metal organometallic compounds for use in the catalyst system in accordance with the present invention are compounds suitable as olefin polymerization catalysts by coordination or insertion polymerization. The class includes known transition organometallic compounds useful in Ziegler-Natta coordination polymerization, such as the group IV metallocene compounds and the late transition metal. These will typically include Group 4–10 transition metal compounds wherein at least one metal ligand can be abstracted by the catalyst activators. As a rule, when said ligand is hydrogen or an hydrocarbyl group containing from 1 to 20 carbon atoms optionally containing silicon atoms, the transition metal organometallic catalyst compounds can be used as such, otherwise an alkylating agent has to be used in order to alkylate said catalyst. The alkylation can be carried out in a separate step or in situ.

The alkylating agent is a compound able to react with the transition metal organometallic catalyst compounds and exchange said ligand that can be abstracted, with an alkyl group. Preferably said alkylating agent is selected from the group consisting of $R^{11}Li$, $R^{11}Na$, $R^{11}K$, $R^{11}MGU$ or $AlR^{11}_{3-z}W_z$, or alumoxanes, wherein $R^{11}$ can be $C_1$–$C_{10}$ alkyl, alkenyl or alkylaryl radicals, optionally containing one or more Si or Ge atoms, z is 0, 1 or 2 or a non integer number ranging from 0 to 2; U is chlorine, bromine or iodine and W is hydrogen or chlorine, bromine or iodine atom; non-limiting examples of $R^{11}$ are methyl, ethyl, butyl and benzyl; non limiting example of $AlR^{11}_{3-z}W_z$ compounds are trimethylaluminum (TMA), tris(2,4,4-trimethyl-pentyl)aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl)aluminum, tris (2-methyl-3-ethyl-pentyl)aluminum and tris(2-ethyl-3,3-dimethyl-butyl). Non limiting example of alumoxanes are: methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

A preferred class of transition metal organometallic compounds are metallocene compounds belonging to the following formula (VIII)

$$(Cp)(ZR^8_m)_n(A)_rML_p \qquad (VIII)$$

wherein $(ZR^8_m)_n$ is a divalent group bridging Cp and A; Z being C, Si, Ge, N or P, and the $R^8$ groups, equal to or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups or two $R^8$ can form a aliphatic or aromatic $C_4$–$C_7$ ring;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;

A is O, S, $NR^9$, $PR^9$ wherein $R^9$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp; M is a transition metal belonging to group 4, 5 or to the lanthanide or actinide groups of the Periodic Table of the Elements (IUPAC version);

the substituents L, equal to or different from each other, are monoanionic sigma ligands selected from the group consisting of hydrogen, halogen, $R^{10}$, $OR^{10}$, $OCOR^{10}$, $SR^{10}$, $NR^{10}_2$ and $PR^{10}_2$, wherein $R^{10}$ is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms; preferably, the substituents L are the same;

m is 1 or 2, and more specifically it is 1 when Z is N or P, and it is 2 when Z is C, Si or Ge;

n is an integer ranging from 0 to 4;

r is 0, 1 or 2; preferably 0 or 1; n is 0 when r is 0;

p is an integer equal to the oxidation state of the metal M minus r+1; i.e. minus 3 when r=2, minus 2 when r=1, and minus 1 when r=0, and ranges from 1 to 4.

In the metallocene compound of formula (VIII), the divalent bridge $(ZR^8_m)_n$ is preferably selected from the group consisting of $CR^8_2$, $(CR^8_2)_2$, $(CR^8_2)_3$, $SiR^8_2$, $GeR^8_2$, $NR^8$ and $PR^8$, $R^8$ having the meaning reported above; more preferably, said divalent bridge is $Si(CH_3)_2$, $SiPh_2$, $CH_2$, $(CH_2)_2$, $(CH_2)_3$ or $C(CH_3)_2$.

The variable m is preferably 1 or 2; the variable n ranges preferably from 0 to 4 and, when n>1, the atoms Z can be the same or different from each other, such as in divalent bridges $CH_2$—O, $CH_2$—S and $CH_2$—$Si(CH_3)_2$.

The ligand Cp, which is π-bonded to said metal M, is preferably selected from the group consisting of cyclopentadienyl, mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 2-methyl indenyl, 3-$^t$butyl-indenyl, 4-phenyl indenyl, 4,5 benzo indenyl; 3-trimethylsilyl-indenyl; 4,5,6,7-tetrahydroindenyl; fluorenyl; 5,10-dihydroindeno[1,2-b]indol-10-yl; N-methyl- or N-phenyl-5,10-dihydroindeno[1,2-b]indol-10-yl; 5,6-dihydroindeno[2,1-b]indol-6-yl; N-methyl-or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl, 2,5-dimethyl-cyclopenta[1,2-b:4,3-b']-dithiophene.

The group A is O, S, $N(R^9)$, wherein $R^9$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, preferably $R^9$ is methyl, ethyl, n-propyl, isopropyl, n-butyl, t-butyl, phenyl, p-n-butyl-phenyl, benzyl, cyclohexyl and cyclododecyl; more preferably $R^9$ is t-butyl; or A has the same meaning of Cp.

Non limiting examples of compounds belonging to formula (VIII) are the rac and meso form (when present) of the following compounds:
bis(cyclopentadienyl)zirconium dimethyl;
bis(indenyl)zirconium dimethyl;
bis(tetrahydroindenyl)zirconium dimethyl;
bis(fluorenyl)zirconium dimethyl;
(cyclopentadienyl)(indenyl)zirconium dimethyl;
(cyclopentadienyl)(fluorenyl)zirconium dimethyl;
(cyclopentadienyl)(tetrahydroindenyl)zirconium dimethyl;
(fluorenyl)(indenyl)zirconium dimethyl;
dimethylsilanediylbis(indenyl)zirconium dimethyl,
dimethylsilanediylbis(2-methyl-4-phenylindenyl)zirconium dimethyl,
dimethylsilanediylbis(4-naphthylindenyl)zirconium dimethyl,
dimethylsilanediylbis(2-methylindenyl)zirconium dimethyl,
dimethylsilanediylbis(2-methyl-4-t-butylindenyl)zirconium dimethyl,
dimethylsilanediylbis(2-methyl-4-isopropylindenyl)zirconium dimethyl,
dimethylsilanediylbis(2,4-dimethylindenyl)zirconium dimethyl,
dimethylsilanediylbis(2-methyl-4,5-benzoindenyl)zirconium dimethyl,
dimethylsilanediylbis(2,4,7-trimethylindenyl)zirconium dimethyl,
dimethylsilanediylbis(2,4,6-trimethylindenyl)zirconium dimethyl,
dimethylsilanediylbis(2,5,6-trimethylindenyl)zirconium dimethyl,
methyl(phenyl)silanediylbis(2-methyl-4,6-diisopropylindenyl)-zirconium dimethyl,
methyl(phenyl)silanediylbis(2-methyl-4-isopropylindenyl)-zirconium dimethyl,
1,2-ethylenebis(indenyl)zirconium dimethyl,
1,2-ethylenebis(4,7-dimethylindenyl)zirconium dimethyl,
1,2-ethylenebis(2-methyl-4-phenylindenyl)zirconium dimethyl,
1,4-butanediylbis(2-methyl-4-phenylindenyl)zirconium dimethyl,
1,2-ethylenebis(2-methyl-4,6-diisopropylindenyl)zirconium dimethyl,
1,4-butanediylbis(2-methyl-4-isopropylindenyl)zirconium dimethyl,
1,4-butanediylbis(2-methyl-4,5-benzoindenyl)zirconium dimethyl,
1,2-ethylenebis (2-methyl-4,5-benzoindenyl)zirconium dimethyl,
[4-($η^5$-cyclopentadienyl)-4,6,6-trimethyl($η^5$-4,5-tetrahydropentalene)]dimethylzirconium,
[4-($η^5$-3'-trimethylsilylcyclopentadienyl)-4,6,6-trimethyl ($η^5$-4,5-tetrahydropentalene)]dimethylzirconium,
(tert-butylamido)(tetramethyl-$η^5$-cyclopentadienyl)-1,2-ethane-dimethyltitanium,
(methylamido)(tetramethyl-$η^5$-cyclopentadienyl)dimethylsilyl-dimethyltitanium,
(methylamido)(tetramethyl-$η^5$-cyclopentadienyl)-1,2-ethanediyl-dimethyltitanium,
(tertbutylamido)-(2,4-dimethyl-2,4-pentadien-1-yl)dimethylsilyl-dimethyltitanium,
bis(1,3-dimethylcyclopentadienyl)zirconium dimethyl,
methylene(3-methyl-cyclopentadienyl)-7-(2,5-dimethylcyclopentadienyl-[1,2-b:4,3-b']dithiophene)zirconium dimethyl;
methylene(3-isopropyl-cyclopentadienyl)-7-(2,5-dimethyl-cyclopentadienyl-[1,2-b:4,3-b']dithiophene)zirconium dimethyl;
methylene(2,4-dimethyl-cyclopentadienyl)-7-(2,5-dimethylcyclopentadienyl-[1,2-b:4,3-b']dithiophene)zirconium dimethyl;
methylene(2,3,5-trimethyl-cyclopentadienyl)-7-(2,5-dimethylcyclopentadienyl-[1,2-b:4,3-b']dithiophene)zirconium dimethyl;
methylene-1-(indenyl)-7-(2,5-dimethylcyclopentadienyl-[1,2-b:4,3-b']dithiophene)zirconium dimethyl;
methylene-1-(indenyl)-7-(2,5-ditrimethylsilylcyclopentadienyl-[1,2-b:4,3-b']dithiophene)zirconium dimethyl;
methylene-1-(3-isopropyl-indenyl)-7-(2,5-dimethylcyclopentadienyl-[1,2-b:4,3-b']dithiophene)zirconium dimethyl;
methylene-1-(2-methyl-indenyl)-7-(2,5-dimethylcyclopentadienyl-[1,2-b:4,3-b']dithiophene)zirconium dimethyl;
methylene-1-(tetrahydroindenyl)-7-(2,5-dimethylcyclopentadienyl-[1,2-b:4,3-b']dithiophene)zirconium dimethyl;
methylene(2,4-dimethyl-cyclopentadienyl)-7-(2,5-dimethylcyclopentadienyl-[1,2-b:4,3-b']dioxazol)zirconium dimethyl;
methylene(2,3,5-trimethyl-cyclopentadienyl)-7-(2,5-dimethylcyclopentadienyl-[1,2-b:4,3-b']dioxazol)zirconium dimethyl;
methylene-1-(indenyl)-7-(2,5-dimethylcyclopentadienyl-[1,2-b:4,3-b']dioxazol)zirconium dimethyl;
isopropylidene(3-methyl-cyclopentadienyl)-7-(2,5-dimethylcyclopentadienyl-[1,2-b:4,3-b']dithiophene)zirconium dimethyl;
isopropylidene(2,4-dimethyl-cyclopentadienyl)-7-(2,5-dimethylcyclopentadienyl-[1,2-b:4,3-b']dithiophene)zirconium dimethyl;
isopropylidene(2,4-diethyl-cyclopentadienyl)-7-(2,5-dimethylcyclopentadienyl-[1,2-b:4,3-b']dithiophene)zirconium dimethyl;
isopropylidene(2,3,5-trimethyl-cyclopentadienyl)-7-(2,5-dimethylcyclopentadienyl-[1,2-b:4,3-b']dithiophene)zirconium dimethyl;
isopropylidene-1-(indenyl)-7-(2,5-dimethylcyclopentadienyl-[1,2-b:4,3-b']dithiophene)zirconium dimethyl;

isopropylidene-1-(2-methyl-indenyl)-7-(2,5-dimethylcyclopentadienyl-[1,2-b:4,3-b']dithiophene)zirconium dimethyl;

dimethylsilandiyl-1-(2-methyl-indenyl)-7-(2,5-dimethylcyclopentadienyl-[1,2-b:4,3-b']dithiophene)hafnium dimethyl;

dimethylsilanediyl(3-tert-butyl-cyclopentadienyl)(9-fluorenyl)zirconium dimethyl, dimethylsilanediyl(3-isopropyl-cyclopentadienyl)(9-fluorenyl)zirconium dimethyl, dimethylsilanediyl(3-methyl-cyclopentadienyl)(9-fluorenyl)zirconium dimethyl, dimethylsilanediyl(3-ethyl-cyclopentadienyl)(9-fluorenyl)zirconium dimethyl, 1-2-ethane(3-tert-butyl-cyclopentadienyl)(9-fluorenyl)zirconium dimethyl, 1-2-ethane(3-isopropyl-cyclopentadienyl)(9-fluorenyl)zirconium dimethyl, 1-2-ethane(3-methyl-cyclopentadienyl)(9-fluorenyl)zirconium dimethyl, 1-2-ethane(3-ethyl-cyclopentadienyl)(9-fluorenyl)zirconium dimethyl, dimethylsilandiylbis-6-(3-methylcyclopentadienyl-[1,2-b]-thiophene) dimethyl;

dimethylsilandiylbis-6-(4-methylcyclopentadienyl-[1,2-b]-thiophene)zirconium dimethyl;

dimethylsilandiylbis-6-(4-isopropylcyclopentadienyl-[1,2-b]-thiophene)zirconium dimethyl;

dimethylsilandiylbis-6-(4-ter-butylcyclopentadienyl-[1,2-b]-thiophene)zirconium dimethyl;

dimethylsilandiylbis-6-(3-isopropylcyclopentadienyl-[1,2-b]-thiophene)zirconium dimethyl;

dimethylsilandiylbis-6-(3-phenylcyclopentadienyl-[1,2-b]-thiophene)zirconium dimethyl;

dimethylsilandiylbis-6-(2,5-dimethyl-3-phenylcyclopentadienyl-[1,2-b]-thiophene)zirconium dimethyl;

dimethylsilandiylbis-6-[2,5-dimethyl-3-(2-methylphenyl)cyclopentadienyl-[1,2-b]-thiophene]zirconium dimethyl;

dimethylsilandiylbis-6-[2,5-dimethyl-3-(2,4,6-trimethylphenyl)cyclopentadienyl-[1,2-b]-thiophene]zirconium dimethyl;

dimethylsilandiylbis-6-[2,5-dimethyl-3-mesitylenecyclopentadienyl-[1,2-b]-thiophene]zirconium dimethyl;

dimethylsilandiylbis-6-(2,4,5-trimethyl-3-phenylcyclopentadienyl-[1,2-b]-thiophene)zirconium dimethyl;

dimethylsilandiylbis-6-(2,5-diethyl-3-phenylcyclopentadienyl-[1,2-b]-thiophene)zirconium dimethyl;

dimethylsilandiylbis-6-(2,5-diisopropyl-3-phenylcyclopentadienyl-[1,2-b]-thiophene)zirconium dimethyl;

dimethylsilandiylbis-6-(2,5-diter-butyl-3-phenylcyclopentadienyl-[1,2-b]-thiophene)zirconium dimethyl;

dimethylsilandiylbis-6-(2,5-ditrimethylsilyl-3-phenylcyclopentadienyl-[1,2-b]-thiophene)zirconium dimethyl;

dimethylsilandiylbis-6-(3-methylcyclopentadienyl-[1,2-b]-silole)zirconium dimethyl;

dimethylsilandiylbis-6-(3-isopropylcyclopentadienyl-[1,2-b]-silole)zirconium dimethyl;

dimethylsilandiylbis-6-(3-phenylcyclopentadienyl-[1,2-b]-silole)zirconium dimethyl;

dimethylsilandiylbis-6-(2,5-dimethyl-3-phenylcyclopentadienyl-[1,2-b]-silole)zirconium dimethyl;

dimethylsilandiylbis-6-[2,5-dimethyl-3-(2-methylphenyl)cyclopentadienyl-[1,2-b]-silole]zirconium dimethyl;

dimethylsilandiylbis-6-[2,5-dimethyl-3-(2,4,6-trimethylphenyl)cyclopentadienyl-[1,2-b]-silole]zirconium dimethyl;

dimethylsilandiylbis-6-[2,5-dimethyl-3-mesitylenecyclopentadienyl-[1,2-b]-silole]zirconium dimethyl;

dimethylsilandiylbis-6-(2,4,5-trimethyl-3-phenylcyclopentadienyl-[1,2-b]-silole)zirconium dimethyl;

[dimethylsilyl(tert-butylamido)][(N-methyl-1,2-dihydrocyclopenta[2,1-b]indol-2-yl)]titanium dimethyl;

[dimethylsilyl(tert-butylamido)][(6-methyl-N-methyl-1,2-dihydrocyclopenta[2,1-b]indol-2-yl)]titanium dimethyl;

[dimethylsilyl(tert-butylamido)][(6-methoxy-N-methyl-1,2-dihydrocyclopenta[2,1-b]indol-2-yl)]titanium dimethyl;

[dimethylsilyl(tert-butylamido)][(N-ethyl-1,2-dihydrocyclopenta[2,1-b]indol-2-yl)]titanium dimethyl;

[dimethylsilyl(tert-butylamido)][(N-phenyl-1,2-dihydrocyclopenta[2,1-b]indol2-yl)]titanium dimethyl;

[dimethylsilyl(tert-butylamido)][(6-methyl-N-phenyl-1,2-dihydrocyclopenta[2,1-b]indol2-yl)]titanium dimethyl;

[dimethylsilyl(tert-butylamido)][(6-methoxy-N-phenyl-1,2-dihydrocyclopenta[2,1-b]indol2-yl)]titanium dimethyl;

[dimethylsilyl(tert-butylamido)][(N-methyl-3,4-dimethyl-1,2-dihydrocyclopenta[2,1-b]indol-2-yl)]titanium dimethyl;

[dimethylsilyl(tert-butylamido)][(N-ethyl-3,4-dimethyl-1,2-dihydrocyclopenta[2,1-b]indol-2-yl)]titanium dimethyl;

[dimethylsilyl(tert-butylamido)][(N-phenyl-3,4-dimethyl-1,2-dihydroclopenta[2,1-b]indol-2-yl)]titanium dimethyl;

as well as the corresponding dichloro, hydrochloro and dihydro compounds and the corresponding $\eta^4$butadiene compounds. When A is $N(R^9)$, a suitable class of metallocene complexes (A) for use in the catalysts complexes of the invention comprises the well-known constrained geometry catalysts, as described in EP-A-0 416 815, EP-A-0 420 436, EP-A-0 671 404, EP-A-0 643 066 and WO-A-91/04257. According to a preferred embodiment of the invention, the group A has the same meaning of Cp, and is preferably substituted or unsubstituted cyclopentadienyl, indenyl, tetrahydroindenyl (2,5-dimethyl-cyclopenta[1,2-b:4,3-b']-dithiophene). Suitable metallocene complexes that may be used in the catalyst system according to the present invention are described in WO 98/22486, WO 99/58539 WO 99/24446, U.S. Pat. No. 5,556,928, WO 96/22995, EP-485822, EP-485820, U.S. Pat. No. 5,324,800 and EP-A-0 129 368. The metal M is preferably Ti, Zr or Hf, and more preferably Zr.

The substituents L are preferably the same and are selected from the group consisting of halogens, $R^{10}$, $OR^{10}$ and $NR^{10}_2$; wherein $R^{10}$ is a $C_1$–$C_7$ alkyl, $C_6$–$C_{14}$ aryl or $C_7$–$C_{14}$ arylalkyl group, optionally containing one or more Si or Ge atoms; more preferably, the substituents L are selected from the group consisting of —Cl, —Br, —Me, —Et, -n-Bu, -sec-Bu, —Ph, —Bz, —CH$_2$SiMe$_3$, —OEt, —OPr, —OBu, —OBz and —NMe$_2$, even more preferably L is methyl.

The integer n ranges from 0 to 4, and it is preferably 1 or 2.

When n=0 and r=1, A can have only the meaning of Cp; Cp and A are preferably pentamethyl cyclopentadienyl, indenyl or 4,5,6,7-tetrahydroindenyl groups.

When n=1 or 2 and r=1, Cp and A, same or different from each other, are preferably cyclopentadienyl, tetramethyl-cyclopentadienyl, indenyl, 4,5,6,7-tetra-hydro-indenyl, 2-methyl-4,5,6,7-tetra-hydro-indenyl, 4,7-dimethyl-4,5,6,7-tetrahydroindenyl, 2,4,7-trimethyl-4,5,6,7-tetra-hydro-indenyl or fluorenyl groups; $(ZR^8_m)_n$ is preferably Me$_2$Si, Me$_2$C, CH$_2$ or C$_2$H$_4$.

Suitable metallocene complexes (A) are the bridged bis-indenyl metallocenes as described for instance in U.S. Pat. No. 5,145,819 and EP-A-0 485 823.

Further metallocene complexes suitable for the catalyst system of the invention are the classes of heterocyclic metallocenes described in WO 98/22486 and WO 99/24446. Among these metallocenes, particularly preferred are the ones reported from page 15, line 8 to page 24, line 17; from page 25, line 1 to page 31, line 9; and from page 58, penultimate line, to page 63, line 20 of WO 98/22486. Other preferred metallocenes are the ones obtained from the bridged ligands listed from page 11, line 18, to page 14, line 13 of WO 99/24446

A further preferred class of transition metal organometallic catalyst compounds are late transition metal complex of formula (IX) or (X)

wherein $M^a$ is a metal belonging to Group 8, 9, 10 or 11 of the Periodic Table of the Elements (new IUPAC notation);

$L^a$ is a bidentate or tridentate ligand of formula (XI):

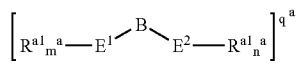

wherein:

D is a $C_1$–$C_{50}$ bridging group linking $E^1$ and $E^2$, optionally containing one or more atoms belonging to Groups 13–17 of the Periodic Table;

$E^1$ and $E^2$, the same or different from each other, are elements belonging to Group 15 or 16 of the Periodic Table and are bonded to said metal $M^a$;

the substituents $R^{a1}$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements (such as B, Al, Si, Ge, N, P, O, S, F and Cl atoms); or two $R^{a1}$ substituents attached to the same atom $E^1$ or $E^2$ form a saturated, unsaturated or aromatic $C_4$–$C_7$ ring, having from 4 to 20 carbon atoms;

$m^a$ and $n^a$ are independently 0, 1 or 2, depending on the valence of $E^1$ and $E^2$, so to satisfy the valence number of $E^1$ and $E^2$; $q^a$ is the charge of the bidentate or tridentate ligand so that the oxidation state of $M^a X^a_p{}^a$ or $M^a A^a$ is satisfied, and the compound (IX) or (X) is overall neutral; $X^a$, the same or different from each other, are monoanionic sigma ligands selected from the group consisting of hydrogen, halogen, $R^a$, $OR^a$, $OSO_2CF_3$, $OCOR^a$, $SR^a$, $-NR^a{}_2$ and $PR^a{}_2$ groups, wherein the $R^a$ substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements (new IUPAC notation), such as B, N, P, Al, Si, Ge, O, S and F atoms; or two $X^a$ groups form a metallacycle ring containing from 3 to 20 carbon atoms; the substituents $X^a$ are preferably the same; $p^a$ is an integer ranging from 0 to 3, so that the final compound (IX) or (X) is overall neutral; and $A^a$ is a π-allyl or a π-benzyl group.

Non limiting examples of late transition metal complexes are those described in WO 96/23010, WO 97/02298, WO 98/40374 and J. Am. Chem. Soc. 120:4049–4050, 1998. Brookhart et al, J. Am. Chem. Soc. 1995, 117, 6414 and Brookhart et al, J. Am. Chem. Soc., 1996, 118, 267, Brookhart et al, J. Am. Chem. Soc. 1998, 120, 4049, Gibson et al, Chem. Commun. 1998, 849, WO 96/27439 and Chem. Ber./Recl. (1997), 130(3), 399–403.

It is a further object of the present invention a process for the polymerization of one or more olefins in the presence of a catalyst system as described above.

The salts according to the invention exert good activities as cocatalysts in olefin polymerization process; moreover, they are easy to prepare. Further they are stable and produce stable catalyst compositions under polymerization conditions.

The molar ratio between the salt (B) and the transition metal organometallic compound (A), calculated as the molar ratio between the Lewis acid and the metal of the transition metal organometallic catalyst compound, preferably ranges from 10:1 to 1:10, more preferably from 2:1 to 1:2, and even more preferably is about 1:1. According to the invention, component (B) can suitably comprise a mixture of two or more salt of the invention. Moreover, component (B) can be used in combination with other compatible cocatalysts known in the state of the art, such as alumoxane compounds. The catalyst system of the invention may also comprise one or more aluminum compounds of formula $AlR^{11}{}_{3-z}W_z$, acting as scavenger, wherein $R^{11}$ can be $C_1$–$C_{10}$ alkyl, alkenyl or alkylaryl radicals, optionally containing one or more Si or Ge atoms, z is 0, 1 or 2 or a non integer number ranging from 0 to 2; U is chlorine, bromine or iodine atom and W is hydrogen, chlorine, bromine or iodine; non-limiting examples of aluminum compounds are trimethylaluminum (TMA), tris(2,4,4-trimethyl-pentyl)aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl) aluminum, tris(2,3-dimethyl-pentyl)aluminum, tris(2,3-dimethyl-heptyl)aluminum, tris(2-methyl-3-ethyl-pentyl) aluminum and tris(2-ethyl-3,3-dimethyl-butyl). Another example of compound that can act as scavenger are alumoxane compounds containing at least one group of the type:

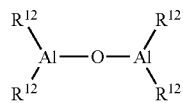

wherein the $R^{12}$ substituents, which may be the same or different, are described above.

In particular, alumoxanes of the formula:

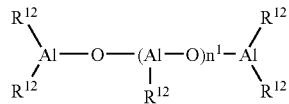

can be used in the case of linear compounds, wherein $n^1$ is 0 or an integer from 1 to 40 and the $R^{12}$ substituents are defined as above, or alumoxanes of the formula:

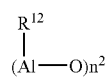

can be used in the case of cyclic compounds, wherein $n^2$ is an integer from 2 to 40 and the $R^{12}$ substituents are defined as above. Examples of alumoxanes suitable as scavenger according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO). Particularly interesting alumoxanes are those disclosed in WO 99/21899.

The catalyst system of the invention may be formed prior to its introduction into a polymerization reactor or in situ in the reactor, by contacting the above-described components (A), (B) and optionally (C). According to an embodiment of the invention, components (A), (B) and optionally (C) are first contacted and then introduced into the reactor, otherwise the component (C) can be separately introduced in the reactor. Alternatively, components (A), (B) and optionally (C) may be contacted together in the reactor. The catalysts of the present invention can be used on inert supports. This may be achieved by depositing said transition metal organometallic compound (A), or the product of the reaction thereof with the salt (B) and optionally with the alkylating agent (C), or said organometallic compound, and subsequently said transition metal organometallic compound before or after the optional treatment with said alkylating agent, on inert supports such as silica, alumina, styrene/divinylbenzene copolymers, polyethylene or polypropylene.

The thus obtained solid compound can be suitably used in gas phase polymerization.

The catalysts of the present invention can be used in the polymerization reactions of olefins. Therefore, according to a further object, the invention provides a process for the polymerization of one or more olefins comprising contacting one or more olefins under polymerization conditions in the presence of a catalyst system as described above.

Olefins which can be polymerized with the process of the present invention are, for instance, α-olefins of formula $CH_2=CHR'$, wherein R' is hydrogen or a $C_1-C_{20}$ alkyl radical.

The catalysts according to the present invention can be conveniently used in the homopolymerization of ethylene, in particular for the preparation of HDPE, and in the copolymerization of ethylene, in particular for the preparation of LLDPE, plastomers or elastomers. Suitable comonomers in ethylene copolymers are α-olefins of formula $CH_2=CHR''$, wherein R'' is a linear, branched or cyclic $C_1-C_{20}$ alkyl radical or cycloolefins. Examples of such olefins are propylene, 1-butene, 1-pentene, 4-methyl-1-pentene, 1-hexene, 1-octene, allyl-cyclohexane, cyclopentene, cyclohexene, norbornene and 4,6-dimethyl-1-heptene. Further suitable comonomers in said ethylene copolymers are polyenes, in particular conjugated or non-conjugated, linear or cyclic dienes, such as 1,4-hexadiene, isoprene, 1,3-butadiene, 1,5-hexadiene and 1,6-heptadiene. When the organometallic compounds object of the present invention are used as cocatalyst in copolymerization of ethylene they generally produce a polymer having a higher molecular weight with respect to alumoxanes, in particular methylalumoxane. The catalysts of the invention can be suitably used in propylene polymerization, for example for the production of isotactic or elastomeric polypropylene.

Moreover, the catalysts of the invention can be suitably used in the preparation of elastomeric copolymers of ethylene with α-olefins of formula $CH_2=CHR'''$, wherein R''' is a $C_1-C_{10}$ alkyl radical, such as propylene, 1-butene, 4-methyl-1-pentene, 1-hexene and 1-octene; said copolymers may optionally contain minor proportions of units deriving from polyenes.

According to a further embodiment, the catalysts according to the present invention are used in the preparation of cycloolefin polymers. Monocyclic and polycyclic olefin monomers can be either homopolymerized or copolymerized, also with linear olefin monomers. The polymerization processes of the present invention can be carried out in liquid phase, optionally in the presence of an inert hydrocarbon solvent, or in gas phase. Said hydrocarbon solvent can be either aromatic (such as toluene) or aliphatic (such as propane, hexane, heptane, isobutane, cyclohexane and 2,2,4-trimethylpentane). The polymerization temperature preferably ranges from 0° C. to 250° C.; in the preparation of HDPE and LLDPE, it is preferably comprised between 20° C. and 150° C. and, more particularly between 40° C. and 90° C.; in the preparation of elastomeric copolymers, it is preferably comprised between 0° C. and 200° C., and more preferably between 20° C. and 100° C. The molecular weight of the polymers can be varied simply by varying the polymerization temperature, the type or the concentration of the catalyst components, or by using molecular weight regulators, such as hydrogen. The molecular weight distribution can be varied by using mixtures of different metallocene complexes or by carrying out the polymerization in several stages which differ in the polymerization temperature and/or the concentrations of molecular weight regulator. The polymerization yield depends on the purity of the transition metal organometallic catalyst compound (A) in the catalyst, therefore, said compound can be used as such or can be subjected to purification treatments before use. The following examples are given for illustrative and not limiting purposes.

GENERAL PROCEDURES AND CHARACTERIZATIONS

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. Indole (Aldrich, purity 98% or Fluka, purity 99%), 2-methylindole (Aldrich, purity 98%), 5-methoxyindole (Aldrich, purity 99%), pyrrole (Aldrich, purity 98%), 2,5-dimethylpyrrole (Aldrich, purity 98%), 2-ethylpyrrole (Aldrich, purity 90%), imidazole (Aldrich, purity 99%) and $B(C_6F_5)_3$ (Boulder Scientific Company) were used as received. Triethylamine (Aldrich, or Fluka, purity 99.5%) was dried over KOH pellets and stored under nitrogen over activated 4 A° molecular sieves before use. The proton and carbon spectra of the compounds were obtained using a Bruker DPX 200 spectrometer operating in the Fourier transform mode at room temperature at 200.13 MHz and 50.33 MHz respectively. The samples were dissolved in $CDCl_3$, $CD_2Cl_2$ or $C_6D_6$. As reference the residual peak of $CHCl_3$, $CHDCl_2$ or $C_6HD_5$ in the $^1H$ spectra (7.25 ppm, 5.35 ppm and 7.15 ppm, respectively) and the peak of the solvent in the $^{13}C$ spectra (53.80 ppm for $CD_2Cl_2$ and 128.00 ppm for $C_6D_6$) were used. Proton spectra were acquired with a 15° pulse and 2 seconds of delay between pulses; 32 transients were stored for each spectrum. The carbon spectra were acquired with a 45° pulse and 6 seconds of delay between pulses; about 512 transients were stored for each spectrum. $CD_2Cl_2$ (Aldrich, 99.8% atom D) was used as received, while $C_6D_6$ (Aldrich, 99% atom D) were dried over activated 4 A° molecular sieves before use. Preparation of the samples was carried out under nitrogen by using standard inert atmosphere techniques.

The melting points of the compounds were obtained by using a capillary Electrothermal instrument.

The intrinsic viscosity (I.V.) was measured in THN at 135° C.

EXAMPLE 1

Synthesis of N-[tris(2,3,4,5,6-pentafluorophenyl)borane]-3H-indole

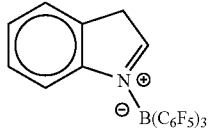

A solution of indole (99%, 0.72 g, MW=117.15, 6.05 mmol) in 5 mL of ethyl ether was added at −20° C. under nitrogen atmosphere to a suspension of tris(2,3,4,5,6-pentafluorophenyl)borane (99.4%, 3.13 g, MW=511.99, 6.07 mmol) in 20 mL of ethyl ether in a 50 mL Schlenk flask. During the addition the colour of the suspension turned from whitish to yellow. The reaction mixture was then allowed to warm up to room temperature and stirred for 2 h with final formation of a yellow solution. A $^1$H NMR analysis showed that the reaction was already complete after 1 h stirring at room temperature. The solvent was evaporated under vacuum to give a light yellow solid as product (yield 100%).

$^1$H NMR (CDCl$_3$, δ, ppm): 4.22 (broad AB system, 2H, H3,H3'); 7.34–7.66 (m, 4H, Ar); 8.77 (d, 1H, J$_{HF}$=5.0 Hz, H2).

Synthesis of triethylammonium of
N-[tris(2,3,4,5,6-pentafluorophenyl)borane]indole
(A-1)

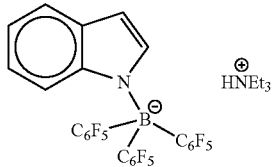

Triethylamine (99.5%, 0.22 mL, MW=101.19, d=0.726, 1.60 mmol) was added dropwise at room temperature under nitrogen atmosphere to a solution of N-[tris(2,3,4,5,6-pentafluorophenyl)borane]-3H-indole (1.01 g, MW=629.14, 1.60 mmol) in 5 mL of dichloromethane in a 25 mL Schlenk flask. During the addition the solution turned from yellow to pink. Exothermicity was not observed. After 1 h stirring at room temperature the solvent was removed under vacuum to give a pinkish solid, which resulted to be the desired product by $^1$H NMR analysis in CD$_2$Cl$_2$ (1.16 g, yield 99.3%).

$^1$H NMR (CD$_2$Cl$_2$, δ, ppm): 1.03 (t, 9H, J=7.3 Hz, N(CH$_2$CH$_3$)$_3$); 2.73 (q, 6H, J=7.3 Hz, N(CH$_2$CH$_3$)$_3$); 4.70 (bs, 1H, NH); 6.33 (m,1H, H3); 6.89–6.98 (m, 2H, Ar); 7.27–7.33 (m, 2H, H2 and Ar); 7.45–7.54 (m, 1H, Ar).

$^{13}$C NMR (CD$_2$Cl$_2$, δ, ppm): 8.77 (N(CH$_2$CH$_3$)$_3$); 47.71 (N(CH$_2$CH$_3$)$_3$); 98.01 (C3); 114.38 (C2); 118.13, 119.20, 120.03 (C4, C5, C6); 130.48 (C3a); 135.26 (C7); 141.17 (C7a).

m.p.=178.6–181.2° C.

EXAMPLE 2

Synthesis of triethylammonium of
N-[tris(2,3,4,5,6-pentafluorophenyl)borane]indole
(A-1) "One Step Process"

Indole (99%, 0.292 g, MW=117.15, 2.47 mmol) and triethylamine (99.5%, 0.252 g, MW=101.19, 2.48 mmol) were dissolved under nitrogen atmosphere into 2 mL of dichloromethane in a 25 mL Schlenk flask. A solution of tris(2,3,4,5,6-pentafluorophenyl)borane (1.26 g, MW=511.99, 2.46 mmol) in 6 mL of dichloromethane was added at 0° C. under stirring. At the end of the addition the yellow solution was allowed to warm up to room temperature and stirred for 17 h. A $^1$H NMR analysis showed that the reaction was already complete after 1 h stirring at room temperature. The solvent was then removed under vacuum to give a pink solid as product, which resulted to be the desired product by NMR analysis (1.54 g, yield 85.7%).

EXAMPLE 3

Synthesis of N-[tris(2,3,4,5,6-pentafluorophenyl)borane]-2-methyl-3H-indole

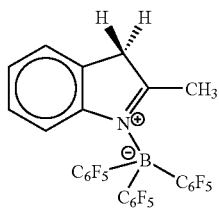

A solution of 2-methylindole (98%, 0.67 g, MW=131.18, 5.01 mmol) in 10 mL of dichloromethane was added at room temperature under nitrogen atmosphere to a solution of tris (2,3,4,5,6-pentafluorophenyl)borane (99.4%, 2.60 g, MW=511.99, 5.05 mmol) in 15 mL of dichloromethane in a 50 mL Schlenk flask. Exothermicity was not observed. During the addition the colour of the solution turned from light orange to orange. A $^1$H NMR analysis in CD$_2$Cl$_2$ showed quantitative conversion of the starting 2-methylindole after 1 h stirring at room temperature. The reaction mixture became a light pink suspension after 4 h stirring at room temperature. The stirring was continued overnight and then the suspension was filtered on a G3 frit. The residue on the frit was a white solid and resulted to be the desired product by $^1$H NMR analysis in C$_6$D$_6$ (2.16 g, yield 67.0%). The final complex is not fully soluble in CD$_2$Cl$_2$, while is fully soluble in C$_6$D$_6$.

$^1$H NMR (C$_6$D$_6$, δ, ppm): 1.70 (m, 3H, CH$_3$); 2.46 (AB system, 2H, J=25.63 Hz, H3,H3'); 6.64–6.83 (m, 3H, Ar); 7.61–7.69 (m, 1H, Ar).

$^{13}$C NMR (C$_6$D$_6$, δ, ppm): 18.77 (dd, J$_{CF}$=9.20 Hz, J$_{CF}$=2.50 Hz, CH$_3$); 46.88 (C3); 117.74 (dd, J$_{CF}$=7.66 Hz, J$_{CF}$=1.84 Hz, C7); 123.83 (Ar); 127.75 (Ar); 128.15 (Ar); 130.79 (C3a); 150.44 (d, J$_{CF}$=3.98 Hz, C7a); 189.36 (C2).

m.p.=204.3–204.5° C.

Synthesis of triethylammonium of N-[tris(2,3,4,5,6-pentafluorophenyl)borane]-2-methylindole (A-2)

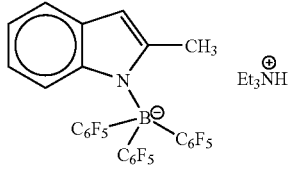

A solution of triethylamine (99.5%, 0.1339 g, MW=101.19, d=0.726, 1.32 mmol) in 10 mL of dichloromethane was added dropwise at room temperature under nitrogen atmosphere to a white suspension of N-[tris(2,3,4,5,6-pentafluorophenyl)borane]-2-methyl-3H-indole (0.8476 g, MW=643.17, 1.32 mmol) in 10 mL of dichloromethane in a 25 mL Schlenk flask. During the addition the white suspension became a light yellow solution. Exothermicity was not observed. A $^1$H NMR analysis in $C_6D_6$ showed complete conversion after 1 h stirring at room temperature. Then after 2 h the solvent was removed under vacuum to give a white solid, which resulted to be the desired product by $^1$H NMR analysis (0.858 g, yield 87.3%).

$^1$H NMR ($C_6D_6$, δ, ppm): 0.20 (t, 9H, J=7.24 Hz, N(CH$_2$CH$_3$)$_3$); 1.64 (q, 6H, J=7.24 Hz, N(CH$_2$CH$_3$)$_3$); 2.39 (bs, 3H, CH$_3$); 6.61–6.78 (m, 2H, CH); 7.04–7.09 (m, 1H, CH); 7.14 (m, 1H, CH); 7.47–7.51 (m, 1H, CH).

$^1$H NMR (CD$_2$Cl$_2$, δ, ppm): 0.99 (t, 9H, J=7.24 Hz, N(CH$_2$CH$_3$)$_3$); 2.23 (bs, 3H, CH$_3$); 2.66 (q, 6H, J=7.24 Hz, N(CH$_2$CH$_3$)$_3$); 4.20 (bs, 1H, NH); 6.17 (bs, 1H, H3); 6.76–6.93 (m, 2H, CH); 7.06–7.10 (m, 1H, CH); 7.36–7.41 (m, 1H, CH).

$^{13}$C NMR (CD$_2$Cl$_2$, δ, ppm): 8.80 (N(CH$_2$CH$_3$)$_3$); 16.41 (dd, J$_{CF}$=6.10 Hz, J$_{CF}$=3.70 Hz, CH$_3$); 47.58 (N(CH$_2$CH$_3$)$_3$); 101.09 (CH); 114.87 (dd, J$_{CF}$=6.10 Hz, J$_{CF}$=1.20 Hz, CH); 117.46 (CH); 117.56 (CH); 118.83 (CH); 130.09(C); 142.96 (C); 146.34(C).

m.p.=87.0–89.2° C.

EXAMPLE 4

Synthesis of N-[tris(2,3,4,5,6-pentafluorophenyl)borane]-5-methoxy-3H-indole

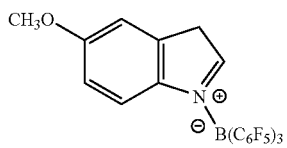

A solution of 5-methoxyindole (99%, 0.78 g, MW=147.18, 5.25 mmol) in 10 mL of CH$_2$Cl$_2$ was added at 0° C. under nitrogen atmosphere to a solution of B(C$_6$F$_5$)$_3$ (99.4%, 2.98 g, MW=511.99, 5.79 mmol) in 20 mL of CH$_2$Cl$_2$ in a 50 mL Schlenk flask. During the addition, the colour of the solution turned immediately from light yellow to yellow. The reaction mixture was allowed to warm up to room temperature and stirred for 2 h, then the solvent was removed under vacuum to give a white powder as product (yield=100%).

$^1$H NMR (CD$_2$Cl$_2$, δ, ppm): 3.86 (s, 3H, OCH$_3$); 4.22 (broad AB system, 2H, H3, H3'); 6.94 (dd, 1H, J=9.11 Hz, J=2.69 Hz, H6); 7.18 (m, 1H, H4); 7.50 (d, 1H, J=9.11 Hz, H7); 8.66 (d, 1H, J=4.83 Hz, H2).

$^{13}$C NMR (CD$_2$Cl$_2$, δ, ppm): 41.99 (C3); 56.20 (OCH$_3$); 110.45 (C4); 115.12 (C6); 118.94 (C7); 135.17 (C3a); 141.43 (C7a); 160.82 (C5); 172.87 (C2).

Synthesis of triethylammonium of N-[tris(2,3,4,5,6-pentafluorophenyl)borane]-5-methoxy]-indole (A-3)

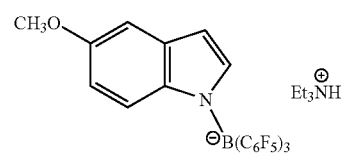

A solution of triethylamine (99.5%, 0.17 g, MW=101.19, d=0.726, 1.70 mmol) in 10 mL of dichloromethane was added dropwise at room temperature under nitrogen atmosphere to a solution of N-[tris(2,3,4,5,6-pentafluorophenyl)borane]-5-methoxy-3H-indole (20817/30, 1.12 g, MW=659.16, 1.70 mmol) in 15 mL of dichloromethane in a 50 mL Schlenk flask. During the addition the solution turned from yellow to pink. Exothermicity was not observed. After 1 h stirring at room temperature the solvent was removed under vacuum to give a pink powder, which resulted to be the desired product by NMR analysis in CD$_2$Cl$_2$ (yield 100%).

$^1$H NMR (CD$_2$Cl$_2$, δ, ppm): 1.06 (t, 9H, J=7.58 Hz, N(CH$_2$CH$_3$)$_3$); 2.85 (q, 6H, J=7.58 Hz, N(CH$_2$CH$_3$)$_3$); 3.80 (s, 1H, OCH$_3$); 4.93 (bs, 1H, NH); 6.26 (bs, 1H, H3); 6.59 (dd, 1H, J=9.05 Hz, J=2.69 Hz, H6); 7.00 (d, 1H, J=2.69 Hz, H4); 7.19 (d, 1H, J=9.05 Hz, H7); 7.31 (bs, 1H, H2).

$^{13}$C NMR (CD$_2$Cl$_2$, δ, ppm): 8.89 (N(CH$_2$CH$_3$)$_3$); 47.89 (N(CH$_2$CH$_3$)$_3$); 56.79 (OCH$_3$); 97.78 (C3); 102.31 (C4); 109.60 (C6); 114.85 (C7); 130.81 (C3a); 135.89 (C2); 136.78 (C7a); 153.06 (C5).

EXAMPLE 5

Synthesis of N-[tris(2,3,4,5,6-pentafluorophenyl)borane]-5H-pyrrole

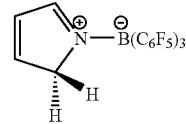

A yellow-orange solution of pyrrole (98%, 0.35 g, MW=67.09, 5.11 mmol) in 10 mL of dichloromethane was added at room temperature under nitrogen atmosphere to a light yellow solution of tris(2,3,4,5,6-pentafluorophenyl)borane (99.4%, 2.64 g, MW=511.99, 5.12 mmol) in 40 mL of dichloromethane in a 100 mL Schlenk flask. Exothermicity was not observed. The so-obtained yellow reaction mixture was stirred for 2 h at room temperature and then the solvent was removed under vacuum to give a white-light yellow powder as product (yield 100%).

$^1$H NMR (CD$_2$Cl$_2$, δ, ppm): 4.71 (bs, 2H, H5,H5'); 6.94 (dq, 1H, J=5.48 Hz, J=1.08 Hz, H3); 7.90 (dq, 1H, J=5.48 Hz, J=1.08 Hz, H4); 8.58 (m, 1H, J=1.08 Hz, H2).

$^{13}$C NMR (CD$_2$Cl$_2$, δ, ppm): 66.72 (m, C5); 128.61 (C3); 156.98 (C4); 172.04 (C2).

NOESY (CD$_2$Cl$_2$): δ$^1$H/δ$^1$H=4.71/7.90 (H5/H4), 7.90/6.94 (H4/H3), 6.94/8.58 (H3/H2).

$^1$H NMR (C$_6$D$_6$, δ, ppm): 3.70 (bs, 2H, H5,H5'); 5.62 (dq, 1H, J=6.16 Hz, J=1.08 Hz, H3); 6.51 (dq, 1H, J=6.16 Hz, J=1.08 Hz, H4); 7.51 (m, 1H, J=1.08 Hz, H2).

$^{13}$C NMR (C$_6$D$_6$, δ, ppm): 65.76 (m, C5); 127.38 (C3); 155.67 (C4); 171.38 (C2).

NOESY (C$_6$D$_6$): δ$^1$H/δ$^1$H=3.70/6.51 (H5/H4), 6.51/5.62 (H4/H3), 5.62/7.51 (H3/H2).

m. p.=187.0° C.–189.6° C.

Synthesis of triethylammonium of
N-[tris(2,3,4,5,6-pentafluorophenyl)borane]pyrrole
(C-1)

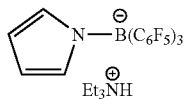

A solution of triethylamine (99.5%, 0.1657 g, MW=101.19, d=0.726, 1.63 mmol) in 5 mL of dichloromethane was added dropwise at room temperature under nitrogen atmosphere to a solution of N-[tris(2,3,4,5,6-pentafluorophenyl)borane]-5H-pyrrole (0.9780 g, MW=579.08, 1.69 mmol) in 12 mL of dichloromethane in a 25 mL Schlenk flask. Exothermicity was not observed. The light yellow solution was stirred for 1 h at room temperature and then the solvent was removed under vacuum to give a whitish solid as product (1.14 g, yield 100%).

$^1$H NMR (CD$_2$Cl$_2$, δ, ppm): 1.27 (t, 9H, J=7.24 Hz, N(CH$_2$CH$_3$)$_3$); 3.03 (q, 6H, J=7.24 Hz, N(CH$_2$CH$_3$)$_3$); 4.85 (bs, 1H, NH); 5.95 (t, 2H, J=2.15 Hz, H3, H4); 6.80 (m, 2H, H2, H5).

$^{13}$C NMR (CDCl$_3$, δ, ppm): 8.46 (N(CH$_2$CH$_3$)$_3$); 46.79 (N(CH$_2$CH$_3$)$_3$); 104.13 (C3, C4); 127.03 (C2, C5).

m.p.=151.1–152.9° C.

EXAMPLE 6

Synthesis of N-[tris(2,3,4,5,6-pentafluorophenyl)borane]-2,5-dimethyl-5H-pyrrole

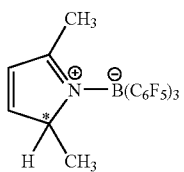

A pink solution of 2,5-dimethylpyrrole (98%, 0.313 g, MW=95.15, 3.22 mmol) in 8 mL of dichloromethane was added at room temperature under nitrogen atmosphere to a light yellow solution of tris(2,3,4,5,6-pentafluorophenyl)borane (99.4%, 1.659 g, MW=511.99, 3.22 mmol) in 15 mL of dichloromethane in a 25 mL Schlenk flask. Exothermicity was not observed. The reaction mixture was stirred for 5 h at room temperature and analysed by $^1$H NMR at different times. The final light orange solution was dried under vacuum giving a yellow powder as product (1.878 g, yield 96.1%). The product resulted to be by NMR analysis a mixture of N-[tris(2,3,4,5,6-pentafluorophenyl)borane]-2,5-dimethyl-5H-pyrrole (90%) and N-[tris(2,3,4,5,6-pentafluorophenyl)borane]-2,5-dimethyl-3H-pyrrole (10%).

m. p.=145.8° C.–146.9° C.

N-[tris(2,3,4,5,6-pentafluorophenyl)borane]-2,5-dimethyl-5H-pyrrole $^1$H NMR (CD$_2$Cl$_2$, δ, ppm): 1.23 (bt, 3H, J=7.14 Hz, CH$_3$ in 5); 2.20 (d, 3H, J=2.84 Hz, CH$_3$ in 2); 5.41 (bs, 1H, H5); 6.62 (dd, 1H, J=5.48 Hz, J=1.17 Hz, H3); 7.67 (m, 1H, J=5.48 Hz, H4).

$^1$H NMR (C$_6$D$_6$, δ, ppm): 0.50 (m, 3H, CH$_3$ in 5); 1.29 (d, 3H, J=2.74 Hz, CH$_3$ in 2); 4.70 (bs, 1H, H5); 5.27 (dd, 1H, J=5.38 Hz, J=1.17 Hz, H3); 6.21 (dm, 1H, J=5.38 Hz, H4).

$^{13}$C NMR (CD$_2$Cl$_2$, δ, ppm): 15.94 (d, J$_{CF}$=15.3 Hz, CH$_3$ in 5); 19.36 (bs, CH$_3$ in 2); 77.02 (d, J$_{CF}$=15.3 Hz, CH5); 130.31 (C3); 161.43 (C4); 185.86 (d, J$_{CF}$=3.70 Hz, C2).

NOESY (CD$_2$Cl$_2$): δ$^1$H/δ$^1$H=5.41/1.23 (H5/CH$_3$ in 5), 2.20/6.62 (CH$_3$ in 2/H3), 6.62/7.67 (H3/H4); 7.67/5.41 (H4/H5).

N-[tris(2, 3,4,5,6-pentafluorophenyl)borane]-2,5-dimethyl-3H-pyrrole $^1$H NMR (CD$_2$Cl$_2$, δ, ppm): 2.03 (bs, 3H, CH$_3$); 2.44 (m, 3H, J=2.05 Hz, CH$_3$); 3.71 (broad AB system, 2H, J=26.8 Hz, H3,H3'); 6.10 (bs, 1H, H4).

$^1$H NMR (C$_6$D$_6$, δ, ppm): 1.53 (m, 3H, CH$_3$); 1.61 (bs, 3H, CH$_3$); 2.09 (broad AB system, 2H, J=27.1 Hz, H3,H3'); 4.98 (bs, 1H, H4).

Synthesis of triethylammonium of N-[tris(2,3,4,5,6-pentafluorophenyl)borane]-2,5-dimethylpyrrole
(A-4)

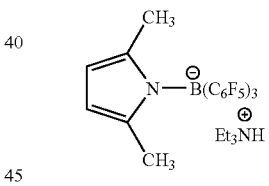

A solution of triethylamine (99.5%, 0.2209 g, MW=101.19, d=0.726, 2.17 mmol) in 5 mL of dichloromethane was added dropwise at room temperature under nitrogen atmosphere to a solution of N-[tris(2,3,4,5,6-pentafluorophenyl)borane]-2,5-dimethyl-5H-pyrrole (1.3080 g, MW=607.14, 2.15 mmol) in 12 mL of dichloromethane in a 25 mL Schlenk flask. Exothermicity was not observed. The yellow solution was stirred for 1 h at room temperature and then the solvent was removed under vacuum to give a yellow-light orange solid as product (yield 100%).

$^1$H NMR (CD$_2$Cl$_2$, δ, ppm): 1.28 (t, 9H, J=7.24 Hz, N(CH$_2$CH$_3$)$_3$); 1.96 (bs, 6H, CH$_3$); 3.06 (q, 6H, J=7.24 Hz, N(CH$_2$CH$_3$)$_3$); 5.68 (bs, 3H, H3, H4, NH).

$^1$H NMR (C$_6$D$_6$, δ, ppm): 0.38 (t, 9H, J=7.24 Hz, N(CH$_2$CH$_3$)$_3$); 1.87 (q, 6H, J=7.24 Hz, N(CH$_2$CH$_3$)$_3$); 2.13 (bs, 6H, CH$_3$); 5.55 (bs, 3H, H3, H4, NH).

$^{13}$C NMR (CD$_2$Cl$_2$, δ, ppm): 8.84 (N(CH$_2$CH$_3$)$_3$); 16.63 (m, CH$_3$); 47.35 (N(CH$_2$CH$_3$)$_3$); 104.69 (C3, C4); 137.29 (C2, C5).

m.p.=119.8–121.5° C.

EXAMPLE 7

Synthesis of N-[tris(2,3,4,5,6-pentafluorophenyl)borane]-2-ethyl-5H-pyrrole

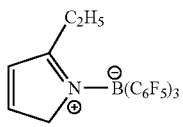

An orange solution of 2-ethylpyrrole (90%, 0.367 g, MW=95.15, 3.47 mmol) in 5 mL of dichloromethane was added at room temperature under nitrogen atmosphere to a light yellow solution of tris(2,3,4,5,6-pentafluorophenyl)borane (99.4%, 1.800 g, MW=511.99, 3.49 mmol) in 15 mL of dichloromethane in a 25 mL Schlenk flask. During the addition the colour of the solution turned immediately from orange to dark orange; exothermicity was not observed. The reaction mixture was stirred overnight at room temperature: a $^1$H NMR analysis showed the presence of ca. 11% mol. of unreacted 2-ethylpyrrole. Then 0.21 g (0.41 mmol) of tris(2,3,4,5,6-pentafluorophenyl)borane were added to complete the reaction. After few minutes stirring, the solvent was removed under vacuum to give a dark yellow powder as product (yield 100%).

$^1$H NMR (CD$_2$Cl$_2$, δ, ppm): 0.88 (t, 3H, J=7.43 Hz, CH$_3$); 2.67 (bm, 2H, CH$_2$); 4.99 (broad AB system, J=25.24 Hz, 2H, H5, H5'); 6.88 (dt, 1H, J=5.58 Hz, J=1.27 Hz, H3); 7.77 (d, 1H, J=5.58 Hz, H4).

$^1$H NMR (C$_6$D$_6$, δ, ppm): 0.075 (t, 3H, J=7.43 Hz, CH$_3$); 2.00 (m, 2H, J=7.43 Hz, CH$_2$); 4.14 (broad AB system, J=25.14 Hz, 2H, H5,H5'); 5.54 (dt, 1H, J=5.48 Hz, J=1.27 Hz, H3); 6.31 (d, 1H, J=5.48 Hz, H4).

$^{13}$C NMR (CD$_2$Cl$_2$, δ, ppm): 9.80 (CH$_3$); 25.48 (CH$_2$); 68.36 (m, C5); 130.30 (C3); 154.37 (C4); 189.38 (C2).

m. p.=185.4° C.–186.8° C.

Synthesis of triethylammonium of N-[tris(2,3,4,5,6-pentafluorophenyl)borane]-2-ethylpyrrole (A-5)

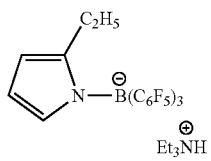

A solution of triethylamine (99.5%, 0.2288 g, MW=101.19, d=0.726, 2.25 mmol) in 6 mL of dichloromethane was added dropwise at room temperature under nitrogen atmosphere to a solution of N-[tris(2,3,4,5,6-pentafluorophenyl)borane]-2-ethyl-5H-pyrrole (1.3518 g, MW=607.14, 2.23 mmol) in 10 mL of dichloromethane in a 25 mL Schlenk flask. Exothermicity was not observed. The orange solution was stirred for 4 h at room temperature and then the solvent was removed under vacuum to give an orange powder as product (1.58 g, yield 100%).

$^1$H NMR (CD$_2$Cl$_2$, δ, ppm): 0.94 (t, 3H, J=8.02 Hz, CH$_3$); 1.28 (t, 9H, J=7.24 Hz, N(CH$_2$CH$_3$)$_3$); 1.94–2.80 (bm, 2H, CH$_2$); 3.07 (q, 6H, J=7.24 Hz, N(CH$_2$CH$_3$)$_3$); 5.89 (bs, 2H, H3, H4); 6.17 (bs, 1H, NH); 6.74 (bs, 1H, H5).

$^{13}$C NMR (CD$_2$Cl$_2$, δ, ppm): 8.74 (N(CH$_2$CH$_3$)$_3$); 13.67 (CH$_3$); 21.24 (CH$_2$); 47.33 (N(CH$_2$CH$_3$)$_3$); 102.24 (C3 or C4); 103.74 (C4 or C3); 126.73 (C5); 142.91 (C2).

EXAMPLE 8

Synthesis of N-ethyl-N-methylanilinium of N-[tris(2,3,4,5,6-pentafluorophenyl)borane]indole (A-6)

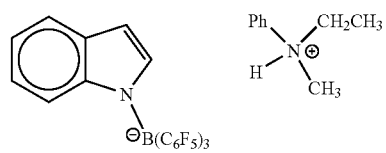

A solution of N-ethyl-N-methylaniline (95%, 0.347 g, MW=135.21, 2.44 mmol) in 7 mL of dichloromethane was added dropwise at room temperature under nitrogen atmosphere to a solution of N-[tris(2,3,4,5,6-pentafluorophenyl)borane]-3H-indole prepared as described above (1.50 g, MW=629.14, 2.38 mmol) in 15 mL of dichloromethane in a 50 mL Schlenk flask. During the addition the solution turned from yellow to light orange. Exothermicity was not observed. After overnight stirring at room temperature a $^1$H NMR analysis showed complete conversion, then the final red amaranthine solution was dried in vacuo to give a fuchsia powder as product (1.71 g, yield 94.0%).

m.p.=59.8–61.9° C.

$^1$H NMR (C$_6$D$_6$, δ, ppm): 0.63 (t, 3H, J=7.09 Hz, N(CH$_2$CH$_3$)); 2.27 (s, 3H, N(CH$_3$)); 2.74 (q, 2H, J=7.09 Hz, N(CH$_2$CH$_3$)); 3.30 (bs, 1H, NH); 6.44–7.64 (m, 11H, CH).

EXAMPLE 9

Synthesis of N-[tris(2,3,4,5,6-pentafluorophenyl)borane]imidazole

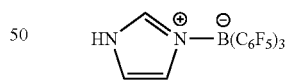

A colourless solution of imidazole (99%, 0.31 g, MW=68.08, 4.50 mmol) in 5 mL of dichloromethane was added at room temperature under nitrogen atmosphere to a light yellow solution of tris(2,3,4,5,6-pentafluorophenyl)borane (2.33 g, MW=511.99, 4.55 mmol) in 13 mL of dichloromethane in a 25 mL Schlenk flask. During the addition the colour of the solution turned from light yellow to yellow. Exothermicity was not observed. The reaction mixture was stirred for 1 h at room temperature and then the solvent was evaporated under vacuum to give a white powder as product (2.60 g, yield 99.6%).

$^1$H NMR (C$_6$D$_6$, δ, ppm): 5.49 (t, 1H, J=1.76 Hz, H5); 6.30 (bs, 1H, H4); 6.66 (bs, 1H, H2); 7.24 (bs, 1H, NH).

NOESY (C₆D₆): δ¹H/δ¹H=7.24/6.66 (NH/H2); 7.24/5.49 (NH/H5); 6.30/5.49 (H4/H5).

¹H NMR (CD₂Cl₂, δ, ppm): 7.18–7.24 (m, 2H, H4 and H5); 8.08 (bs, 1H, H2); 10.05 (bs, 1H, NH).

¹³C NMR (CD₂Cl₂, δ, ppm): 117.81 (C5); 126.66 (C4); 136.22 (C2).

m.p.=214.9° C.–217.8° C.

Synthesis of triethylammonium of N-[tris(2,3,4,5,6-pentafluorophenyl)borane]imidazole (C-2)

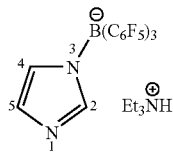

A solution of triethylamine (99.5%, 0.231 g, MW=101.19, d=0.726, 2.27 mmol) in 5 mL of dichloromethane was added dropwise at room temperature under nitrogen atmosphere to a solution of N-[tris(2,3,4,5,6-pentafluorophenyl)borane] imidazole (1.254 g, MW=580.07, 2.16 mmol) in 15 mL of dichloromethane in a 25 mL Schlenk flask. During the addition the colour of the solution turned from light yellow to yellow and exothermicity was not observed. After overnight stirring at room temperature, a ¹H NMR analysis in CD₂Cl₂ showed complete conversion of the starting material, then the solvent was removed in vacuo to give a white powder as product (1.35 g, purity 99%, yield 90.8%).

¹H NMR (CD₂Cl₂, δ, ppm): 1.27 (t, 9H, J=7.24 Hz, N(CH₂CH₃)₃); 3.01 (q, 6H, J=7.24 Hz, N(CH₂CH₃)₃); 6.93 (t, 1H, J=1.47 Hz, H4 or H5); 7.00 (bs, 1H, H5 or H4); 7.62 (m, 1H, H2); 13.76 (m, 1H, NH).

¹³C NMR (CD₂Cl₂, δ, ppm): 9.02 (N(CH₂CH₃)₃); 45.82 (N(CH₂CH₃)₃); 121.92 (C4 or C5); 125.44 (C4 or C5); 138.89 (C2).

POLYMERIZATION EXAMPLES 1–3 AND COMPARATIVE POLYMERIZATION EXAMPLES 4–5

2 L of hexane were loaded into a 4.25-L stainless-steel stirred reactor at 30° C., followed by TIBA in hexane (amounts specified in Table 1) as a scavenger. Propylene and ethylene were then pressurized into the reactor, to reach the composition of 1.2 wt % ethylene and 22.8 wt % propylene, and the temperature of the reactor was then raised up to 60° C.

The catalyst system was prepared by dissolving 5 mg of ind₂ZrMe₂ in 5 mL toluene, and then quickly adding the cocatalyst indicated in table 1 in 5 mL toluene (Zr/cocat molar ration 1:1). The polymerization was started by injecting the toluene solution containing catalyst system into the autoclave at the polymerization temperature, by means of ethylene overpressure, then the temperature was maintained at the polymerization temperature, and ethylene was continuously fed into the reactor in order to maintain a constant pressure. After 40 g of ethylene were added, the polymerization was stopped by pressurizing 1.5 L of CO into the reactor, venting and cooling the reactor. Inactive tests are stopped after 60 min. The ethylene/propylene amorphous copolymer was recovered from the hexane solution by precipitation in acetone, followed by drying under reduced atmosphere at 70° C. for 4 hours. The polymerization data are listed in Table 1.

TABLE 1

| Pol. Ex. | Salt | TIBA, mg | TIBA, mmol | time min | kg/g_cat | kg/(g_cat xh) | ethylene % wt (NMR) | I.V dL/g. |
|---|---|---|---|---|---|---|---|---|
| 1 | A-1 | 10.4 | 3 | 12 | 14.8 | 74.0 | 75.6 | 2.02 |
| 2 | A-3 | 10.8 | 3 | 24 | 12.2 | 30.5 | 80.2 | 2.50 |
| 3 | A-5 | 10.06 | 3 | 18 | 12.6 | 42.0 | 78.4 | 2.13 |
| 4 comp. | C-1 | 9.7 | 3 | 60 | 0 | 0 | — | — |
| 5 comp. | C-2 | 9.7 | 3 | 60 | 0 | 0 | — | — |

The invention claimed is:

1. A salt of formula (I)

$$[HE°R^1_3]^+[T^1T^2]^- \quad (I)$$

wherein

E° is a nitrogen or phosphorous atom;

R¹, equal to or different from each other, are selected from the group consisting of linear and branched, saturated and unsaturated, C₁–C₃₀ alkyl, C₆–C₂₀ aryl, C₇–C₂₀ arylalkyl and C₇–C₂₀ alkylaryl groups, optionally containing O, S, N, P, Si or halogen atoms, or two R¹ form one C₄–C₇ ring, optionally containing O, S, N, P or Si atoms that optionally bear substituents;

T¹ is a Lewis acid that forms a complex with T², T¹ having formula (II)

$$MtR^2_3 \quad (II)$$

wherein

Mt is an element belonging to Group 13 of the Periodic Table of the Elements (IUPAC);

R², equal to or different from each other, are selected from the group consisting of halogen, halogenated C₆–C₂₀ aryl and halogenated C₇–C₂₀ alkylaryl groups; two R² groups can also form with the element Mt one condensed ring;

$T^2$ is a moiety of formula (III)

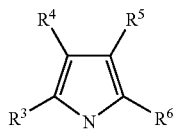

wherein
$R^3$, $R^4$, $R^5$ and $R^6$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that optionally bear substituents; with the proviso that at least one of the $R^3$, $R^4$, $R^5$ and $R^6$ is different from hydrogen.

2. The salt according to claim 1 wherein $R^1$ is selected from the group consisting of linear and branched, saturated and unsaturated, $C_1$–$C_{30}$ alkyl; and $E^o$ is nitrogen.

3. The salt according to claim 1 wherein in formula (II) Mt is B or Al; the substituents $R^2$ are selected from the group consisting of $C_6F_5$, $C_6F_4H$, $C_6F_3H_2$, $C_6H_3(CF_3)_2$, perfluorobiphenyl, heptafluoro-naphthyl, hexafluoro-naphthyl and pentafluoro-naphthyl.

4. The salt according to claim 1 wherein $T^2$ has formula (IV):

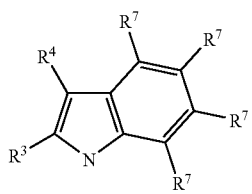

wherein
the substituents $R^3$ and $R^4$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or $R^3$ and $R^4$ form one $C_4$–$C_7$ ring, optionally containing O, S, N, P or Si atoms, that optionally bear substituents; and the substituents $R^7$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups optionally containing O, S, N, P, Si or halogen atoms, or two or more adjacent substituents $R^7$ form one or more $C_4$–$C_7$ rings optionally containing O, S, N, P or Si atoms, said rings optionally bearing substituents.

5. A process for preparing a salt of formula (I)

$$[HE^oR^1{}_3]^+[T^1T^2]^- \quad (I)$$

wherein $E^o$ is a nitrogen or phosphorous atom;
$R^1$, equal to or different from each other, are selected from the group consisting of linear and branched, saturated and unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^1$ can form one $C_4$–$C_7$ ring, optionally containing O, S, N, P or Si atoms, that bear substituents;
$T^1$ is a Lewis acid that forms a complex with $T^2$, $T^1$ having formula (II)

$$MtR^2{}_3 \quad (II)$$

wherein Mt is an element belonging to Group 13 of the Periodic Table of the Elements (IUPAC);
$R^2$, equal to or different from each other, are selected from the group consisting of halogen, halogenated $C_6$–$C_{20}$ aryl and halogenated $C_7$–$C_{20}$ alkylaryl groups; two $R^2$ groups can also form with the element Mt one condensed ring;
$T^2$ is a moiety of formula (III)

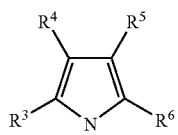

wherein $R^3$, $R^4$, $R^5$ and $R^6$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that optionally bear substituents; with the proviso that at least one of the $R^3$, $R^4$, $R^5$ and $R^6$ is different from hydrogen, comprising the step of contacting:
i) about one equivalent of a compound of formula (V)

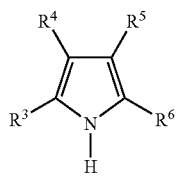

wherein $R^3$, $R^4$, $R^5$ and $R^6$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that optionally bear substituents; with the proviso that at least one of $R^3$, $R^4$, $R^5$ and $R^6$ is different from hydrogen;
ii) about one equivalent of the Lewis acid of formula (II); and
iii) about one equivalent of a compound of formula $E^oR^1{}_3$;
wherein $E^o$ is a nitrogen or phosphorous atom;
$R^1$, equal to or different from each other, are selected from the group consisting of linear and branched, saturated and unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^1$ can form one $C_4$–$C_7$ ring, optionally containing O, S, N, P or Si atoms, that optionally bears at least one substituent.

6. The process according to claim 5 comprising the following steps:
   a) contacting about one equivalent of the compound of formula (V) with one equivalent of the Lewis acid of formula (II); and
   b) optionally isolating a reaction product of step a) and then adding about one equivalent of the compound of formula $E^oR^1_3$.

7. A catalyst system for the polymerization of olefins comprising a product obtained by contacting:
   (A) at least one transition metal organometallic compound;
   (B) a salt of formula (I)

$$[HE^oR^1_3]^+[T^1T^2]^- \quad (I)$$

wherein
   $E^o$ is a nitrogen or phosphorous atom;
   $R^1$, equal to or different from each other, are selected from the group consisting of linear and branched, saturated and unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^1$ optionally form one $C_4$–$C_7$ ring, optionally containing O, S, N, P or Si atoms, that optionally bear substituents;
   $T^1$ is a Lewis acid that forms a complex with $T^2$, $T^1$ having formula (II)

$$MtR^2_3 \quad (II)$$

wherein Mt is an element belonging to Group 13 of the Periodic Table of the Elements (IUPAC);
   $R^2$, equal to or different from each other, are selected from the group consisting of halogen, halogenated $C_6$–$C_{20}$ aryl and halogenated $C_7$–$C_{20}$ alkylaryl groups; two $R^2$ groups can also form with the element Mt one condensed ring;
   $T^2$ is a moiety of formula (III)

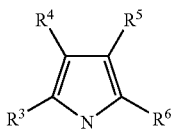

(III)

wherein $R^3$, $R^4$, $R^5$ and $R^6$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that optionally bears substituents; with the proviso that at least one of $R^3$, $R^4$, $R^5$ and $R^6$ is different from hydrogen; and
   (C) optionally an alkylating agent.

8. The catalyst system according to claim 7 wherein the transition metal organometallic compound has formula (VIII)

$$(Cp)(ZR^8_m)_n(A)_rML_p \quad (VIII)$$

wherein
   $(ZR^8_m)_n$ is a divalent group bridging Cp and A;
   Z is C, Si, Ge, N or P; and
   the $R^8$ groups, equal to or different from each other, are hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups, or two $R^8$ optionally form an aliphatic or aromatic $C_4$–$C_7$ ring;
   Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;
   A is O, S, $NR^9$, or $PR^9$ wherein $R^9$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;
   M is a transition metal belonging to group 4, 5 or to the lanthanide or actinide groups of the Periodic Table of the Elements (IUPAC version);
   the substituents L, equal to or different from each other, are monoanionic sigma bonding ligands selected from the group consisting of hydrogen, halogen, $R^{10}$, $OR^{10}$, $OCOR^{10}$, $SR^{10}$, $NR^{10}_2$ and $PR^{10}_2$, wherein $R^{10}$ is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms;
   m is 1 when Z is N or P, and m is 2 when Z is C, Si or Ge;
   n is an integer ranging from 0 to 4;
   r is 0, 1 or 2;
   n is 0 when r is 0; and
   p is an integer equal to the oxidation state of the metal M minus r+1 and ranges from 1 to 4.

9. The catalyst system according to claim 7 wherein the transition metal organometallic compound has formulas (IX) or (X)

$$L^aM^aX^a_p \quad (IX) \quad L^aM^aA^a \quad (X)$$

wherein
   $M^a$ is a metal belonging to Group 8, 9, 10 or 11 of the Periodic Table of the Elements (new IUPAC notation);
   $L^a$ is a bidentate or tridentate ligand of formula (XI):

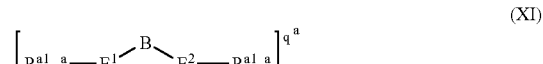

(XI)

wherein:
   D is a $C_1$–$C_{50}$ bridging group linking $E^1$ and $E^2$, optionally containing one or more atoms belonging to Groups 13–17 of the Periodic Table;
   $E^1$ and $E^2$, the same or different from each other, are elements belonging to Group 15 or 16 of the Periodic Table and are bonded to said metal $M^a$;
   the substituents $R^{a1}$, equal to or different from each other, are selected from the group consisting of hydrogen, linear and branched, saturated and unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more atoms belonging to groups 13–17 of the Periodic Table of the Elements; or two $R^{a1}$ substituents, attached to the same atom $E^1$ or $E^2$, form a saturated, unsaturated or aromatic $C_4$–$C_7$ ring, having from 4 to 20 carbon atoms;
   $m^a$ and $n^a$ are independently 0, 1 or 2, depending on the valence of $E^1$ and $E^2$, so as to satisfy the valence number of $E^1$ and $E^2$; $q^a$ is the charge of the bidentate or tridentate ligand so that the oxidation state of $M^a X^a_p{}^a$ or $M^a A^a$ is satisfied, and the compound (IX) or (X) is overall electrically neutral;

$X^a$, the same or different from each other, are monoanionic sigma bonding ligands selected from the group consisting of hydrogen, halogen, $R^a$, $OR^a$, $OSO_2CF_3$, $OCOR^a$, $SR^a$, —$NR^a{}_2$ and $PR^a{}_2$ groups, wherein the $R^a$ substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements (new IUPAC notation); or two $X^a$ groups form a metallacycle ring containing from 3 to 20 carbon atoms;

$p^a$ is an integer ranging from 0 to 3, so that the final compound (IX) or (X) is overall electrically neutral; and $A^a$ is a n-allyl or a n-benzyl group.

10. A process for the polymerization of one or more olefins comprising contacting one or more olefins under polymerization conditions in the presence of a catalyst system comprising a product obtained by contacting:

(A) at least one transition metal organometallic compound;
(B) a salt of formula (I)

$$[HE^oR^1{}_3]^+[T^1T^2]^-  \qquad (I)$$

wherein $E^o$ is a nitrogen or phosphorous atom;

$R^1$, equal to or different from each other, are selected from the group consisting of linear and branched, saturated and unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^1$ can form one $C_4$–$C_7$ ring, optionally containing O, S, N, P or Si atoms that optionally bear substituents;

$T^1$ is a Lewis acid that forms a complex with $T^2$, $T^1$ having formula (II)

$$MtR^2{}_3 \qquad (II)$$

wherein Mt is an element belonging to Group 13 of the Periodic Table of the Elements (IUPAC);

$R^2$, equal to or different from each other, are selected from the group consisting of halogen, halogenated $C_6$–$C_{20}$ aryl and halogenated $C_7$–$C_{20}$ alkylaryl groups; two $R^2$ groups can also form with the element Mt one condensed ring;

$T^2$ is a moiety of formula (III)

wherein $R^3$, $R^4$, $R^5$ and $R^6$, equal to or different from each other, are selected from the group consisting of hydrogen, halogen, linear and branched, saturated and unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^3$, $R^4$, $R^5$ and $R^6$ form one or more $C_4$–$C_7$ rings, optionally containing O, S, N, P or Si atoms, that optionally bear substituents; with the proviso that at least one of $R^3$, $R^4$, $R^5$ and $R^6$ is different from hydrogen; and (C) optionally an alkylating agent.

11. The catalyst system according to claim 9 wherein the $X^a$, the same as each other, are monoanionic sigma ligands selected from the group consisting of hydrogen, halogen, $R^a$, $OR^a$, $OSO_2CF_3$, $OCOR^a$, $SR^a$, —$NR^a{}_2$ and $PR^a{}_2$ groups, wherein the $R^a$ substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements (new IUPAC notation); or two $X^a$ groups form a metallacycle ring containing from 3 to 20 carbon atoms.

12. The catalyst system according to claim 8 wherein r is 0 or 1.

* * * * *